USiv008652034B2

(12) United States Patent
Metcalf, Jr. et al.

(10) Patent No.: US 8,652,034 B2
(45) Date of Patent: Feb. 18, 2014

(54) SURGICAL INSTRUMENT STABILIZER AND METHOD

(75) Inventors: Newton H. Metcalf, Jr., Memphis, TN (US); Gregory C. Marik, Collierville, TN (US); Danish Siddiqui, Northbrook, IL (US); Amanda D. Vanover, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 237 days.

(21) Appl. No.: 13/252,522

(22) Filed: Oct. 4, 2011

(65) Prior Publication Data
US 2013/0085340 A1 Apr. 4, 2013

(51) Int. Cl.
*A61B 1/32* (2006.01)
(52) U.S. Cl.
USPC .......................... 600/210; 600/206; 600/207
(58) Field of Classification Search
USPC ......................................... 606/206, 207, 210
See application file for complete search history.

(56) References Cited

U.S. PATENT DOCUMENTS

| 4,545,374 | A | 10/1985 | Jacobson |
|---|---|---|---|
| 4,668,222 | A | 5/1987 | Poirier |
| 5,279,575 | A | 1/1994 | Sugarbaker |
| 5,540,648 | A | 7/1996 | Yoon |
| 5,897,531 | A | 4/1999 | Amirana |
| RE36,702 | E | 5/2000 | Green |
| 6,228,068 | B1 | 5/2001 | Yoon |
| 6,355,028 | B2 | 3/2002 | Castaneda et al. |
| 6,478,029 | B1 | 11/2002 | Boyd et al. |
| 7,118,576 | B2 | 10/2006 | Gitis et al. |
| 7,608,065 | B2 | 10/2009 | Glenn |
| 7,691,089 | B2 | 4/2010 | Gresham |
| 7,806,870 | B2 | 10/2010 | Mastri et al. |
| 7,972,310 | B2 | 7/2011 | Kessler |
| 2010/0057010 | A1 | 3/2010 | Goeransson |
| 2011/0124969 | A1* | 5/2011 | Stopek ........................ 600/206 |

FOREIGN PATENT DOCUMENTS

| WO | 9832380 | | 7/1998 |
|---|---|---|---|
| WO | 0108563 | A3 | 2/2001 |
| WO | 0230352 | A3 | 4/2002 |

OTHER PUBLICATIONS

Synthes, Technique Guide "Insight Tubes. Tubular Minimal Invasiveaccess System." May 31, 2010 http://www.synthes.com/sites/intl/IntlContent/Files/036.001.035.pdf.

(Continued)

*Primary Examiner* — Andrew Yang
(74) *Attorney, Agent, or Firm* — Sorell Lenna & Schmidt LLP

(57) ABSTRACT

A surgical instrument stabilizer includes a body having a first material and a second material. The first material includes a wall defining an inner surface and an outer surface. The inner surface defines a first cavity configured for disposal of the second material. The outer surface defines an outer portion, a lateral portion and an inner portion. At least a portion of the lateral portion is configured to flexibly conform to a patient body surface. The inner portion defines a second cavity for disposal of an instrument and is configured to engage an outer surface of the instrument. Methods of use are disclosed.

19 Claims, 3 Drawing Sheets

(56) References Cited

OTHER PUBLICATIONS

Gordon R. Haddow, John M. Toomasian, Christina T. Mora Mangano, Cardiopulmonary Bypass for Port-Access Cardiac Surgery, Chapter 35: Cardiopulmonary Bypass for Port-Access Cardiac Surgery, http://www.wildcatanesthesia.com/Lippincott%20Interactive%20CD/text/gr/gr035.htm.

Colorado Comprehensive Spine Institute, Minimal Access Spinal Surgery: What Is It All About? http://www.coloradospineinstitute.com/subject.php?pn=treatment-minimal-access-53.

* cited by examiner

SURGICAL INSTRUMENT STABILIZER AND METHOD

TECHNICAL FIELD

The present disclosure generally relates to medical devices, systems and methods employed during surgical applications, and more particularly, to a surgical system that includes a device to control position, orientation and/or stability of a surgical instrument.

BACKGROUND

Minimally invasive surgical procedures including percutaneous techniques are known that have attempted to overcome the above drawbacks of open surgery. Minimally invasive surgical procedures minimize disruption and trauma to the body to reduce recovery time and post-operative pain. For example, minimally invasive surgical techniques are employed for spinal and neurosurgical applications to access surgical sites within the body adjacent vital intervening tissues, in an effort to avoid damaging such vital tissues.

Surgical instruments, such as a penetrating sleeve, cannula or guide, pass through tissue walls of the body to gain access to anatomical cavities and provide access to a surgical site for surgical treatment of, for example, spinal disorders including fusion, fixation, discectomy, laminectomy and implantable prosthetics. Such instruments can be stabilized and oriented to maintain position for access to tissue and other body structures under treatment within the anatomical cavity. This disclosure describes an improvement over these prior art technologies.

SUMMARY OF THE INVENTION

Accordingly, a surgical instrument stabilizer is provided that includes a device that controls position, orientation and/or stability of a surgical instrument. It is contemplated that the surgical instrument stabilizer may be employed with percutaneous and minimally invasive procedures for treating spinal disorders.

In one particular embodiment, in accordance with the principles of the present disclosure, a surgical instrument stabilizer is provided. The surgical instrument stabilizer includes a body including a first material and a second material. The first material includes a wall defining an inner surface and an outer surface. The inner surface defines a first cavity configured for disposal of the second material. The outer surface defines an outer portion, a lateral portion and an inner portion. At least a portion of the lateral portion is configured to flexibly conform to a patient body surface. The inner portion defines a second cavity for disposal of an instrument and is configured to engage an outer surface of the instrument.

In one embodiment, the surgical instrument stabilizer includes a membrane including a wall defining an inner surface and an outer surface. The inner surface defines a closed cavity. The outer surface defines an outer portion, a lateral portion and an inner portion. At least a portion of the lateral portion is configured to conform to at least non-uniform and undulating surfaces of a patient body surface. The inner portion defines a central cavity configured for disposal of an elongated instrument and is configured to engage an outer surface of the instrument. A moldable material is configured for disposal in the closed cavity. The inner portion is disposable between a first configuration such that the inner portion flexibly supports the instrument and a second configuration such that the inner portion rigidly supports the instrument.

In one embodiment, a surgical system is provided that includes a toroid body including a wall defining an inner surface and an outer surface. The inner surface defines a closed cavity. The outer surface defines an outer portion, a lateral portion and an inner portion. At least a portion of the lateral portion is configured to conform to at least non-uniform and undulating surfaces of a patient body surface. The inner portion defines a central cavity. A moldable material is configured for disposal in the closed cavity. An elongated drill guide is configured for disposal within the central cavity of an elongated instrument. The inner portion is disposable between a first configuration such that the inner portion engages an outer surface of the drill guide to flexibly support the drill guide for positioning and orientation, and a second configuration such that the moldable material engages the inner surface to dispose the inner portion into fixed engagement with the outer surface of the drill guide such that the inner portion rigidly supports the drill guide.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION OF THE INVENTION

Figure 1:
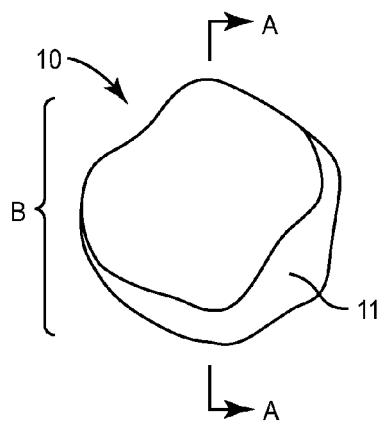
FIG. 1 is a perspective view of one embodiment of a surgical instrument stabilizer in accordance with the principles of the present disclosure.
Figure 2:
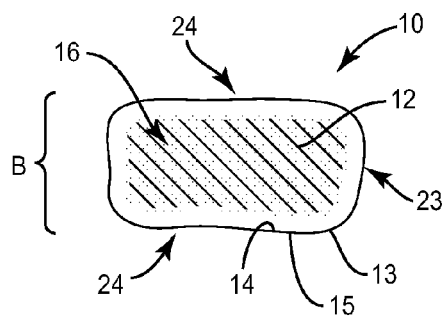
FIG. 2 is a side cross section view of the surgical instrument stabilizer taken along lines A-A in FIG. 1.

The exemplary embodiments of the surgical instrument stabilizer and related methods of use disclosed are discussed in terms of medical devices for the treatment of musculoskeletal disorders and more particularly, in terms of a surgical system including a surgical instrument stabilizer that controls position, orientation and/or stability of a surgical instrument, such as, for example, a retractor instrument, tube, sleeve, cannula and/or drill guide. It is contemplated that the surgical system is configured to support a surgical instrument, which is used, for example, with a minimally invasive surgical procedure. It is envisioned that the surgical system and methods of use disclosed provide a stabilizing mount that conforms to a surface of a patient to minimize undesired movement of a surgical instrument. It is further envisioned that the surgical instrument stabilizer is low profile to a patient allowing a surgeon facile access to a surgical site. In one embodiment, one or all of the components of the surgical system can be disposable. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-9, there is illustrated components of a surgical system, which includes a surgical instrument stabilizer 10 in accordance with the principles of the present disclosure.

The components of the surgical system can be fabricated from biologically acceptable materials suitable for medical applications, including synthetic polymers, depending on the particular application and/or preference of a medical practitioner. For example, the components of the surgical system, individually or collectively, can be fabricated from materials such as polymeric rubbers, polyethylene terephthalate (PET), fabric, silicone, polyurethane, silicone-polyurethane copolymers, polymeric rubbers, polyolefin rubbers, hydrogels, semi-rigid materials, elastomers, rubbers, thermoplastic elastomers, thermoset elastomers, elastomeric composites. Various components of the surgical instrument stabilizer may have material composites, including the above materials, to achieve various desired characteristics such as strength, rigidity, elasticity, compliance, biomechanical performance, durability and radiolucency or imaging preference. The components of the surgical system, individually or collectively, may also be fabricated from a heterogeneous material such as a combination of two or more of the above-described materials. The components of the surgical system may be monolithically formed, integrally connected or include fastening elements and/or instruments, as described herein.

The surgical system including surgical instrument stabilizer 10 is employed, for example, in minimally invasive surgical procedures, including percutaneous surgical techniques for controlling position, orientation and/or stability of a surgical instrument. For example, surgical instrument stabilizer 10 can be used with a retractor tube or sleeve for control and stability thereof, a delivery sleeve or cannula for delivering implants and/or a drill guide for facilitating fastening of bone fasteners with tissue, such as, for example, bone.

The surgical instrument stabilizer 10 has a body B including a first material, such as, for example, a membrane 11 and a second material 12. The membrane 11 includes a wall 13 defining an inner surface 14 and an outer surface 15. The inner surface 14 defines a first cavity, such as, for example, a chamber 16 configured for disposal of the second material 12.

Figure 3:
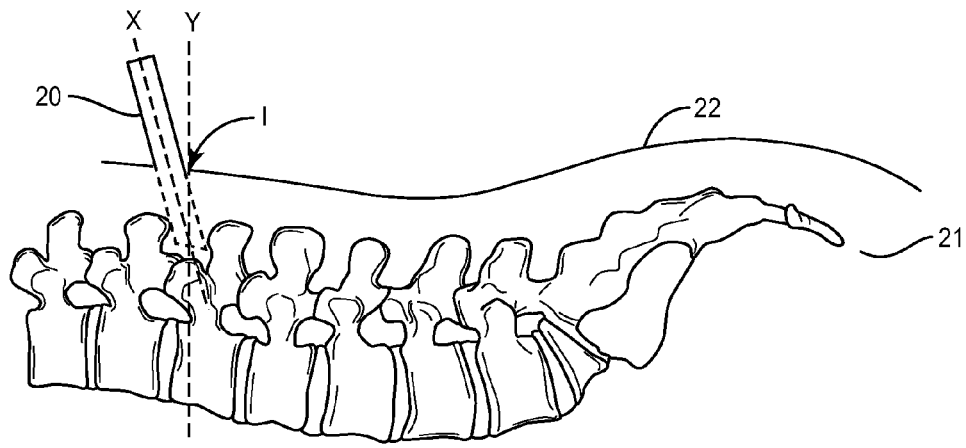
FIG. 3 is a side view, in part cross section, of a surgical instrument disposed adjacent a surgical site of a patient.
Figure 4:
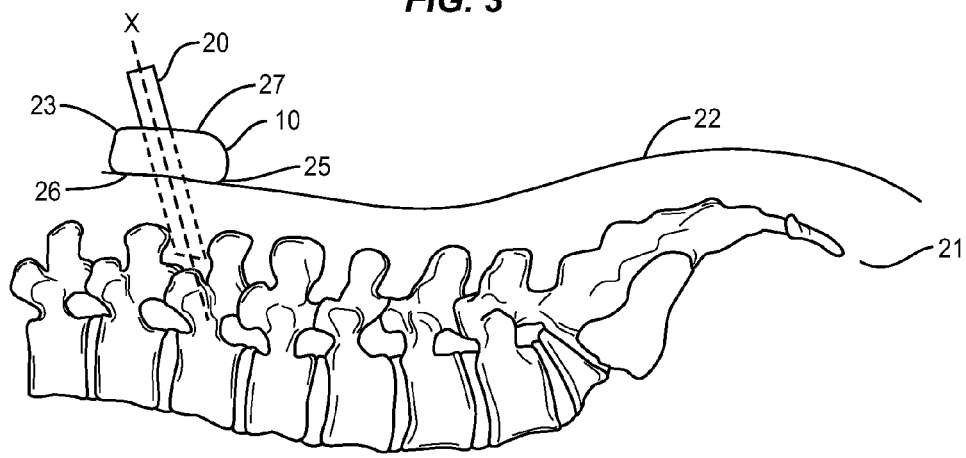
FIG. 4 is a side view, in part cross section, of the surgical instrument stabilizer shown in FIG. 1 and the surgical site shown in FIG. 3.
Figure 5:
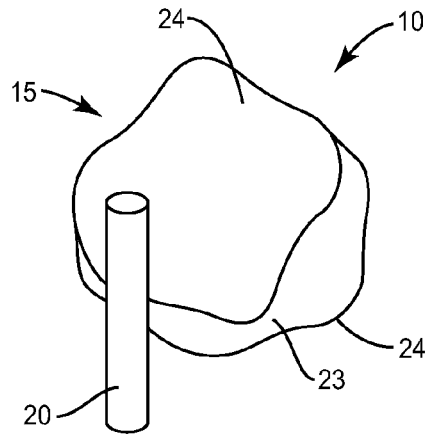
FIGS. 5-9 are perspective views illustrating the use of the surgical instrument stabilizer shown in FIG. 1.
Figure 6:
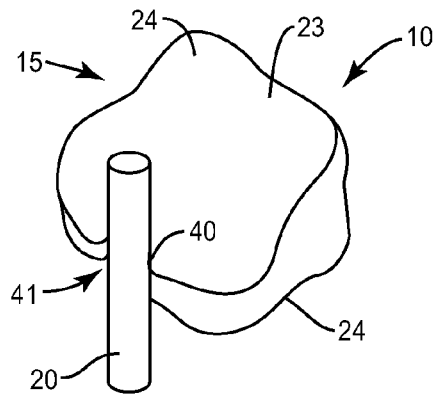
Figure 7:
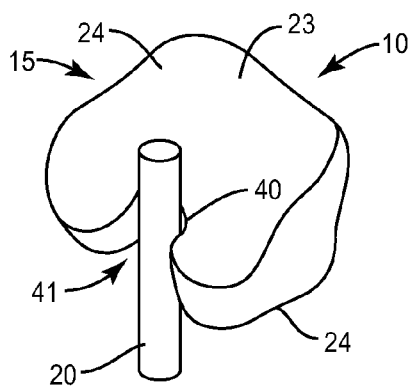
Figure 8:
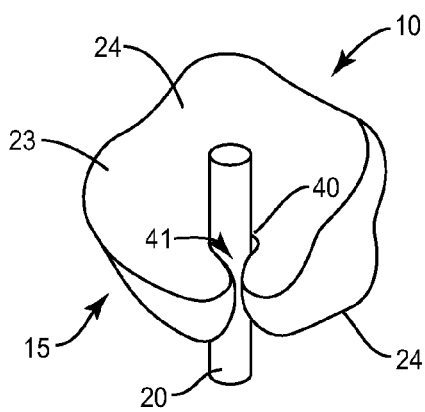

Body B has a substantially malleable and flexible configuration for conforming to the surface of a patient body (FIGS. 3 and 4). In a first configuration, such as, for example, a flexible configuration, body B is supported on a surface, such as, for example, the outer surface of a patient, surgical instruments, pads, sheets and/or bedding. Body B engages an outer surface of a surgical instrument, such as, for example, a retractor tube 20, as will be described. In this flexible configuration, retractor tube 20 is flexibly supported for positioning and orientation relative to a surgical site. Body B is engageable and/or manipulated to a second configuration, such as, for example, a fixed or rigid support configuration such that the second material 12 is moldable to dispose outer surface 15 into fixed engagement with the outer surface of the retractor tube 20 for rigid support thereof in a predetermined and/or selected orientation. It is envisioned that body B, in the first or second configurations, may have alternate cross section configurations, such as, for example, oval, oblong, triangular, rectangular, square, polygonal, irregular, uniform, non-uniform, variable and/or tapered. It is further envisioned that manipulation of body B to the fixed or rigid configuration may include manual, electrical, magnetic and/or mechanical engagement and/or stimulation.

Membrane 11 of the surgical instrument stabilizer 10 is designed to be flexible and relatively inelastic. Membrane 11 of the surgical instrument stabilizer 10 can be fabricated from biologically acceptable materials suitable for medical applications, including, but not limited to polyethylene, latex and polyurethane. Other materials with similar properties are contemplated.

The second material 12 of the surgical instrument stabilizer 10 is designed to be malleable, but capable of maintaining its form when molded into a particular shape. The second material 12 of the surgical instrument stabilizer 10 can be fabricated from various materials, including a granular material such as sand, clay, memory foam, a magnetic locking material with granular ferrous insert material, polyethylene, latex and polyurethane. Other materials with similar properties are contemplated.

The first cavity 16 defined within the inner surface 14 of the wall 13 encloses and contains the second material 12. It is contemplated that membrane 11 flexibly conforms to a configuration of the second material 12. It is also contemplated that membrane 11 is fabricated from a different material relative to the second material 12.

The outer surface 15 of body B defines an outer portion 23, a lateral portion 24 and an inner portion 40, as shown in FIGS. 5-9. Lateral portion 24 is configured to flexibly conform to a patient body surface 22 at interface 25 (FIG. 4). Lateral portion 24 includes a first side 26 configured to conform to a patient body surface 22 and a second side 27. It is contemplated that the lateral portion 24 is configured to flexibly conform to at least non-uniform and undulating surfaces of the patient body surface 22. It is envisioned that all or only a portion of outer surface 15 may have alternate surface configurations, such as, for example, rough, threaded for connection with other instruments, arcuate, undulating, porous, semi-porous, dimpled, polished and/or textured according to the requirements of a particular application.

In assembly, operation and use, as shown in FIGS. 3 and 4, the surgical system including surgical instrument stabilizer 10 is employed, for example, with a minimally invasive surgical procedure for spinal and neurosurgical applications with a patient. For example, during minimally invasive spine surgery, a surgeon will make a small incision I, typically less than one inch, in the skin of a patient's back over vertebrae to be treated. One or more dilators may be employed to gradually separate the muscles and create a portal through which the surgery may be performed.

A retractor assembly and/or retractor tube 20 is positioned adjacent the surgical site over the small incision I. Retractor tube 20 is passed through the incision I to create a passageway or portal to the surgical site. Retractor tube 20 is disposed with the incision I in an unsupported configuration. The surgical instrument stabilizer 10 is employed to augment the surgical procedure to control the position and orientation of retractor tube 20 as well as provide stability to retractor tube 20 during the surgical procedure.

Body B is manipulated for disposal about the outer surface of retractor tube 20, as schematically shown in FIGS. 5-9. Interface 25 of side 26 flexibly conforms to the surfaces of the patient body surface 22 including the non-uniform and undulating surfaces. It is envisioned that interface 25 may conform to various surfaces of the patient body surface 22 including various tissue surfaces, planar surfaces and/or surgical instrumentation surfaces, such as, for example, padding, linens, bed rails, mounting members and surgical articulation equipment.

Upon disposal of body B about the outer surface of retractor tube 20, the outer portion 23 is manipulated to form inner portion 40, which is configured to engage the outer surface of retractor tube 20, as shown in FIGS. 5-8. Inner portion 40 defines a second cavity 41 for disposal of the retractor tube 20. In a first configuration, such as, for example, a flexible support configuration, the inner portion 40 flexibly supports the retractor tube 20 for positioning and orentation. In the flexible support configuration, retractor tube 20 may be positioned, repositioned and/or adjusted, to one or a plurality of orientations in a plurality of reference axes relative to a surgical site.

Retractor tube 20 is introduced through incision I (FIG. 3) along an axis y adjacent a surgical site. From its alignment with axis y, retractor tube 20 is movably positioned in a selected orientation to a selected x axis relative to axis y adjacent the surgical site. From the flexible support configuration of body B and inner portion 40, outer surface 15 is manipulated such that material 12 is molded, via engagement, stimulation and/or manipulation, depending on the material 12 employed, to dispose body B and inner portion 40 to a fixed or rigid support configuration to support retractor tube 20 in the selected orientation in alignment with axis x.

Figure 9:
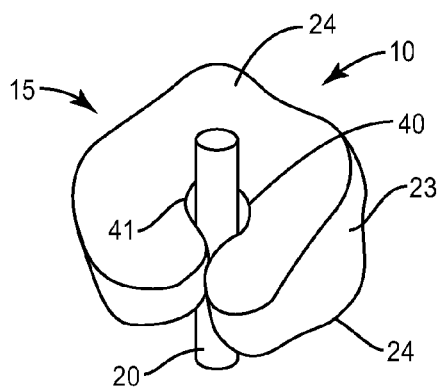

Material 12 engages inner portion 40 to change its configuration to the fixed or rigid support configuration and dispose inner portion 40 into fixed engagement with the outer surface of retractor tube 20 such that inner portion fixedly and/or rigidly supports retractor tube 20, as shown in FIG. 9. It is contemplated that retractor tube 20, fixedly supported by body B, may be disposed at alternate axial orientations relative to axis y, for example, perpendicular and/or other angular orientations such as acute or obtuse, co-axial, parallel and/or may be offset or staggered.

It is contemplated that material 12 can be molded to dispose body B and inner portion 40 to a fixed or rigid configuration with various materials, forms of engagement and/or stimulation. In one embodiment, material 12 includes a granular material such as sand, which is manipulated, massaged, kneaded or engaged to dispose inner portion 40 into fixed engagement with the outer surface of retractor tube 20 such that inner portion rigidly supports retractor tube 20. In one embodiment, material 12 includes a clay substance and/or a memory foam material, which is manipulated, or engaged to dispose inner portion 40 into fixed engagement with the outer surface of retractor tube 20 such that inner portion rigidly supports retractor tube 20. In one embodiment, material 12 includes magnetic memory material such that a magnetic field, electric current and/or electromagnetic field is passed through material 12 to dispose inner portion 40 into fixed engagement with the outer surface of retractor tube 20 such that inner portion rigidly supports retractor tube 20. It is contemplated that the material 12 can be a surgical grade ferrous material.

It is also contemplated that other methods of providing additional fixed support for retractor tube 20 can be incorporated into the system. For example, the use of a magnetic push pin lock configuration can provide added fixed support to retractor tube 20. In one embodiment, a Steinmen pin can be delivered to a surgical site for attachment to a facet and be positioned along the retractor tube 20 within inner portion 40.

It is envisioned that the use of microsurgical and image guided technologies may be employed to access, view and repair spinal deterioration or damage, with the aid of surgical instrument stabilizer 10. Upon completion of the procedure, the surgical instruments and assemblies are removed and the incision is closed. It is envisioned that surgical instrument stabilizer 10 may be employed with an open spine surgery and/or a mini-open surgery and percutaneous surgical implantation.

It is contemplated that a surgical procedure may employ other instruments that can be mounted with surgical instrument stabilizer 10, such as, for example, nerve root retractors, tissue retractors, forceps, cutter, drills, scrapers, reamers, separators, rongeurs, taps, cauterization instruments, irrigation and/or aspiration instruments, illumination instruments and/or inserter instruments.

Surgical instrument stabilizer 10 may be employed for performing spinal surgeries, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners.

Figure 10:
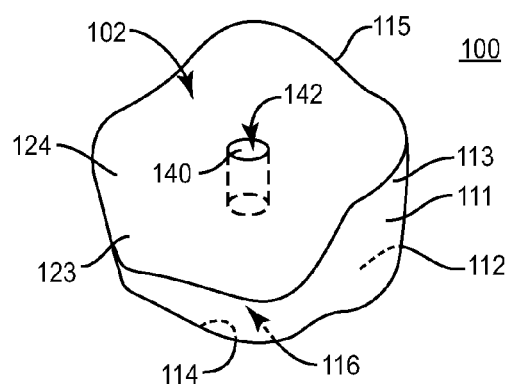
FIG. 10 is a perspective view of one embodiment of a surgical instrument stabilizer in accordance with the principles of the present disclosure.
Figure 11:
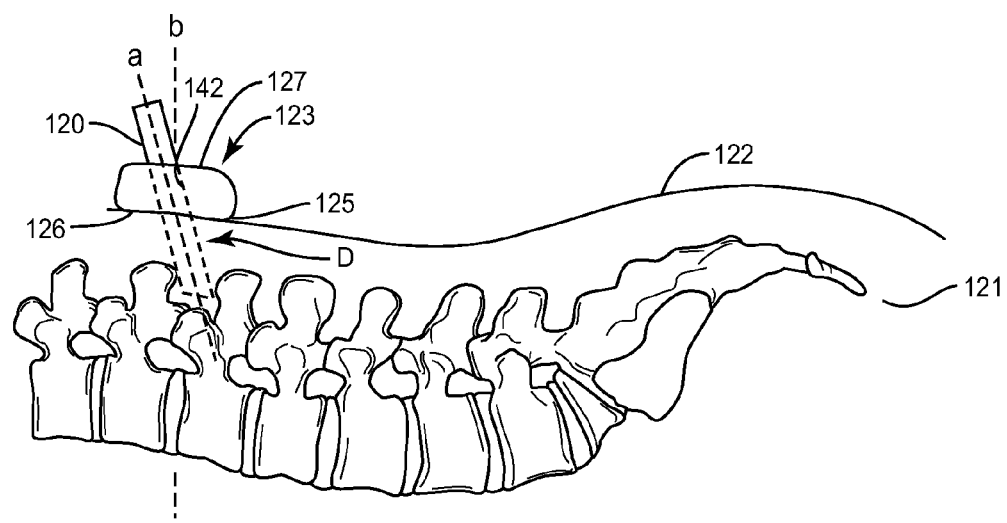
FIG. 11 is a side view, in part cross section, of the surgical instrument stabilizer shown in FIG. 10 and a surgical instrument disposed adjacent a surgical site.

In one embodiment, as shown in FIGS. 10-11, the surgical system, similar to that described above with regard to FIGS. 1-9, includes a surgical instrument stabilizer 100 having a body 102. Body 102 has a toroid configuration and includes a membrane 111 and a second material 112. The membrane 111 includes a wall 113 defining an inner surface 114 and an outer surface 115. The inner surface 114 defines a closed cavity 116 configured for disposal of the second material 112.

Body 102 has a substantially malleable and flexible configuration for conforming to the surface of a patient body (FIG. 11). In a first configuration, such as, for example, a flexible configuration, body 102 is supported on a surface 122 of a patient. Body 102 engages an outer surface of a drill guide 120. In this flexible configuration, drill guide 120 is flexibly supported for positioning and orientation relative to a surgical site. Body 102 is engageable and/or manipulated to a fixed or rigid support configuration such that the second material 112 is moldable to dispose outer surface 115 into fixed engagement with the outer surface of the retractor tube 20 for rigid support thereof in a predetermined and/or selected orientation, similar to that described above.

The outer surface 115 defines an outer portion 123, a lateral portion 124 and an inner portion 140. Inner portion 140 defines a central cavity 142 configured for disposal of a surgical instrument, such as, for example, drill guide 120. Lateral portion 124 is configured to flexibly conform to a patient body surface 122 at an interface 125. Lateral portion 124 includes a first side 126 configured to conform to patient body surface 122 and a second side 127. It is contemplated that the lateral portion 124 is configured to flexibly conform to at least non-uniform and undulating surfaces of the patient body surface 122.

In assembly, operation and use, the surgical system including surgical instrument stabilizer 100 is employed with a minimally invasive surgical procedure, similar to those described herein. The surgical instrument stabilizer 100 is employed to augment the surgical procedure to control the position and orientation of drill guide 120 as well as provide stability to drill guide 120 during the surgical procedure.

Body 102 is manipulated for disposal with the patient adjacent the surgical site. Interface 125 of side 126 flexibly conforms to the surfaces of the patient body surface 122 including the non-uniform and undulating surfaces. Drill guide 120 is passed through central cavity 142 to adjacent the surgical site. Drill guide 120 is disposed with the incision I, along an axis b, in an unsupported configuration. Inner portion 140 is configured to engage the outer surface of drill guide 120. In a flexible support configuration, the inner portion 40 flexibly supports the drill guide 120 for positioning and orientation. In the flexible support configuration, drill guide 120 may be positioned, repositioned and/or adjusted, to one or a plurality of orientations in a plurality of reference axes relative to a surgical site.

From its alignment with axis b, drill guide 120 is movably positioned in a selected orientation to a selected axis a relative to axis b adjacent the surgical site. From the flexible support configuration of body 102 and inner portion 140, outer surface 115 is manipulated such that material 112 is molded, via engagement, stimulation and/or manipulation, depending on the material 112 employed, to dispose body 102 and inner portion 140 to a fixed or rigid support configuration to support drill guide 120 in the selected orientation in alignment with axis a.

Material 112 engages inner portion 140 to change its configuration to the fixed or rigid support configuration and dispose inner portion 140 into fixed engagement with the outer surface of drill guide 120 such that inner portion 140 fixedly and/or rigidly supports drill guide 120. It is contemplated that drill guide 120, fixedly supported by body 102, may be disposed at alternate axial orientations relative to axis y, for example, perpendicular and/or other angular orientations such as acute or obtuse, co-axial, parallel and/or may be offset or staggered.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An instrument stabilizer comprising:
    a body including a first material and a second material,
    the first material including a wall defining an inner surface and an outer surface, the inner surface defining a first cavity configured for disposal of the second material,
    the outer surface defining an outer portion, a lateral portion and an inner portion, at least a portion of the lateral portion being configured to flexibly conform to a patient body surface and the inner portion defining a second cavity for disposal of an instrument and being configured to engage an outer surface of the instrument, wherein the inner portion is disposable between a first configuration such that the inner portion flexibly supports the instrument and a second configuration such that the inner portion rigidly supports the instrument.

2. The instrument stabilizer of claim 1, wherein a magnetic field is applied to the second material such that the second material engages the first material to dispose the inner portion in the second configuration.

3. The instrument stabilizer of claim 1, wherein said body is configured to wrap around said instrument to provide the rigid support for said instrument.

4. The instrument stabilizer of claim 1, wherein the second cavity includes a passageway configured for slidable movement of the instrument therethrough relative to the inner portion in the first configuration.

5. The instrument stabilizer of claim 1, wherein the first material flexibly conforms to a configuration of the second material.

6. The instrument stabilizer of claim 1, wherein the first material is different from the second material.

7. The instrument stabilizer of claim 1, wherein the second cavity defines a longitudinal axis and the inner portion is configured to support the instrument in the second cavity in a range of 0-90 degrees relative to the longitudinal axis.

8. The instrument stabilizer of claim 1, wherein the body has a toroid configuration.

9. The instrument stabilizer of claim 1, wherein the second material includes a malleable clay compound.

10. The instrument stabilizer of claim 1, wherein the second material includes a granular material.

11. The instrument stabilizer of claim 1, wherein the lateral portion is configured to flexibly conform to at least non-uniform and undulating surfaces of the patient body surface.

12. An instrument stabilizer comprising:
    a membrane including a wall defining an inner surface and an outer surface, the inner surface defining a closed cavity, the outer surface defining an outer portion, a lateral portion and an inner portion, at least a portion of the lateral portion being configured to conform to at least non-uniform and undulating surfaces of a patient body surface, and the inner portion defining a central cavity configured for disposal of an elongated instrument and being configured to engage an outer surface of the instrument; and a moldable material configured for disposal in the closed cavity, wherein the inner portion is disposable between a first configuration such that the inner portion flexibly supports the instrument and a second configuration such that the inner portion rigidly supports the instrument.

13. The instrument stabilizer of claim 12, wherein the central cavity defines a longitudinal axis and the inner portion is configured to support the instrument in the second cavity in a range of 0-90 degrees relative to the longitudinal axis.

14. The instrument stabilizer of claim 12, wherein the central cavity includes a passageway configured for slidable movement of the instrument therethrough relative to the inner portion in the first configuration.

15. The instrument stabilizer of claim 12, wherein said body is configured to wrap around said instrument to provide the rigid support for said instrument.

16. The instrument stabilizer of claim 12, wherein a magnetic field is applied to the moldable material such that the moldable material engages the membrane to dispose the inner portion in the second configuration.

17. The instrument stabilizer of claim 12, wherein the membrane has a toroid configuration.

18. The instrument stabilizer of claim 12, wherein the instrument is a drill guide.

19. A spinal surgical system comprising:

a toroid body including a wall defining an inner surface and an outer surface, the inner surface defining a closed cavity, the outer surface defining an outer portion, a lateral portion and an inner portion, at least a portion of the lateral portion being configured to conform to at least non-uniform and undulating surfaces of a patient body surface, and the inner portion defining a central cavity;

a moldable material configured for disposal in the closed cavity; and an elongated drill guide configured for disposal within the central cavity of an elongated instrument, wherein the inner portion is disposable between a first configuration such that the inner portion engages an outer surface of the drill guide to flexibly support the drill guide for positioning and orientation, and a second configuration such that the moldable material engages the inner surface to dispose the inner portion into fixed engagement with the outer surface of the drill guide such that the inner portion rigidly supports the drill guide.

* * * * *